(12) United States Patent
Taszreak

(10) Patent No.: US 8,926,711 B2
(45) Date of Patent: Jan. 6, 2015

(54) PROSTHETICS USING CURVED DAMPENING CYLINDERS

(71) Applicant: College Park Industries, Inc., Warren, MI (US)

(72) Inventor: Aaron Taszreak, China, MI (US)

(73) Assignee: College Park Industries, Inc.

( * ) Notice: Subject to any disclaimer, the term of this patent is extended or adjusted under 35 U.S.C. 154(b) by 0 days.

(21) Appl. No.: 13/783,808

(22) Filed: Mar. 4, 2013

(65) Prior Publication Data

US 2014/0249652 A1    Sep. 4, 2014

(51) Int. Cl.
| | |
|---|---|
| *A61F 2/72* | (2006.01) |
| *A61F 2/64* | (2006.01) |
| *A61F 2/66* | (2006.01) |
| *A61F 2/68* | (2006.01) |
| *A61F 2/50* | (2006.01) |
| *A61F 2/74* | (2006.01) |

(52) U.S. Cl.
CPC ............... *A61F 2/6607* (2013.01); *A61F 2/68* (2013.01); *A61F 2002/5006* (2013.01); *A61F 2002/745* (2013.01); *A61F 2002/748* (2013.01)
USPC .............................................. 623/26; 623/47

(58) Field of Classification Search
CPC ........... A61F 2/6607; A61F 2002/5006; A61F 2002/5035; A61F 2002/5033
USPC .................. 623/26, 47, 48, 50, 56, 49, 51–55
See application file for complete search history.

(56) References Cited

U.S. PATENT DOCUMENTS

| | | | |
|---|---|---|---|
| 2,470,480 A | 5/1949 | Fogg | |
| 2,567,393 A | 9/1951 | Haller | |
| 5,948,021 A * | 9/1999 | Radcliffe | ........................ 623/44 |
| 5,957,981 A * | 9/1999 | Gramnas | ........................ 623/47 |
| 6,182,697 B1 * | 2/2001 | Parker et al. | ............. 137/625.16 |
| 6,443,993 B1 | 9/2002 | Koniuk | |
| 6,855,170 B2 | 2/2005 | Gramnas | |
| 7,029,500 B2 | 4/2006 | Martin | |

(Continued)

OTHER PUBLICATIONS

Nieuwendijk, J., A new type of body-powered prosthesis, Delft University of Technology, (believed to have been offered for sale, publicly used and/or published prior to the filing date of this application).

(Continued)

*Primary Examiner* — Thomas J Sweet
*Assistant Examiner* — Christie Bahena
(74) *Attorney, Agent, or Firm* — Gifford, Krass, Sprinkle, Anderson & Citkowski, P.C.

(57) ABSTRACT

Prosthetic joint and limb components utilize a single, curved dampening cylinder to reduce component count and wear. A prosthetic foot/ankle requires only three major components; namely, a housing adapted for coupling to a foot blade, an ankle component adapted for coupling to a pylon, and a piston that moves within a curved cylinder in the housing during ambulation. The ankle component is pivotally attached to the housing at the center of curvature of the cylinder. The piston defines front and rear, variable volume chambers in the cylinder. The chambers are in fluid communication with one another via a port, such that fluid is exchanged between the chambers through one-way check valves as the ankle pivots between plantarflexion and dorsiflexion. Fluid flow is independently adjustable to establish and maintain desired levels of dampening during plantarflexion and dorsiflexion, including different levels of dampening.

12 Claims, 10 Drawing Sheets

(56) References Cited

U.S. PATENT DOCUMENTS

| | | |
|---|---|---|
| RE39,961 E | 12/2007 | Petrofsky et al. |
| 7,341,603 B2 | 3/2008 | Christensen |
| 7,942,935 B2 | 5/2011 | Iversen et al. |
| 7,955,398 B2 | 6/2011 | Bedard et al. |
| 7,985,265 B2 | 7/2011 | Moser et al. |
| 8,206,458 B1 * | 6/2012 | Hawkins .................. 623/26 |
| 2005/0203639 A1 | 9/2005 | Wild |
| 2009/0204229 A1 | 8/2009 | Mosler et al. |
| 2012/0130508 A1 * | 5/2012 | Harris et al. ............... 623/50 |

OTHER PUBLICATIONS

Asiabanpour, B. et al., Mobile Paving System (MPS): A New Large Scale Freeform Fabrication Method, Aug. 23, pp. 19-30, 2005.

* cited by examiner

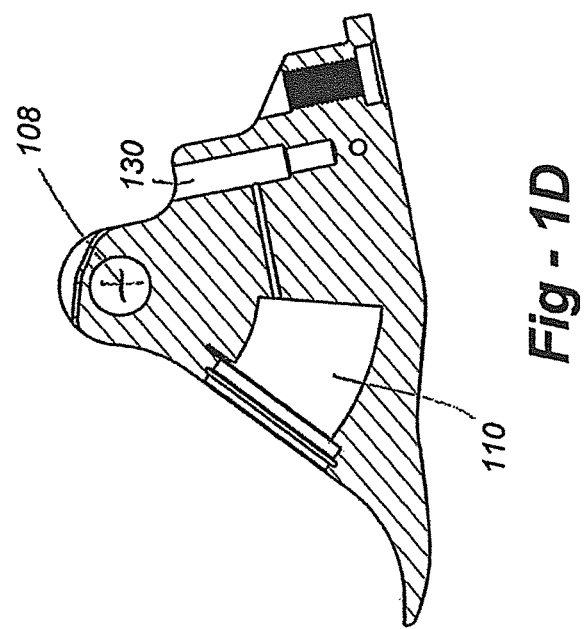
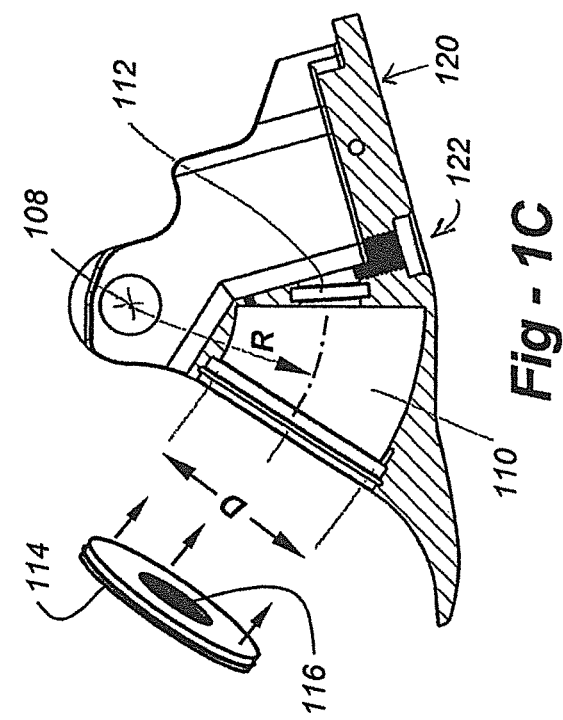
Fig - 1D
Fig - 1C

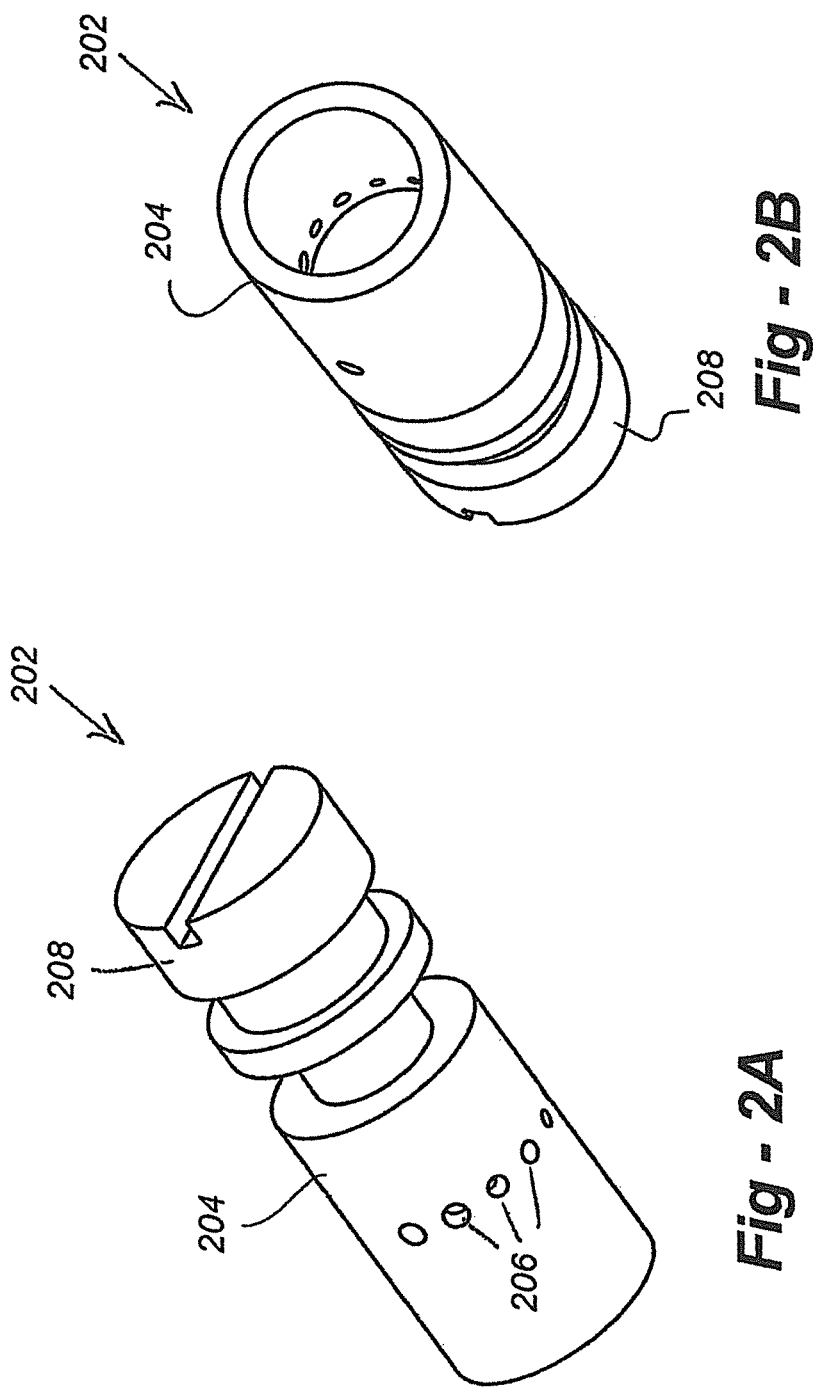

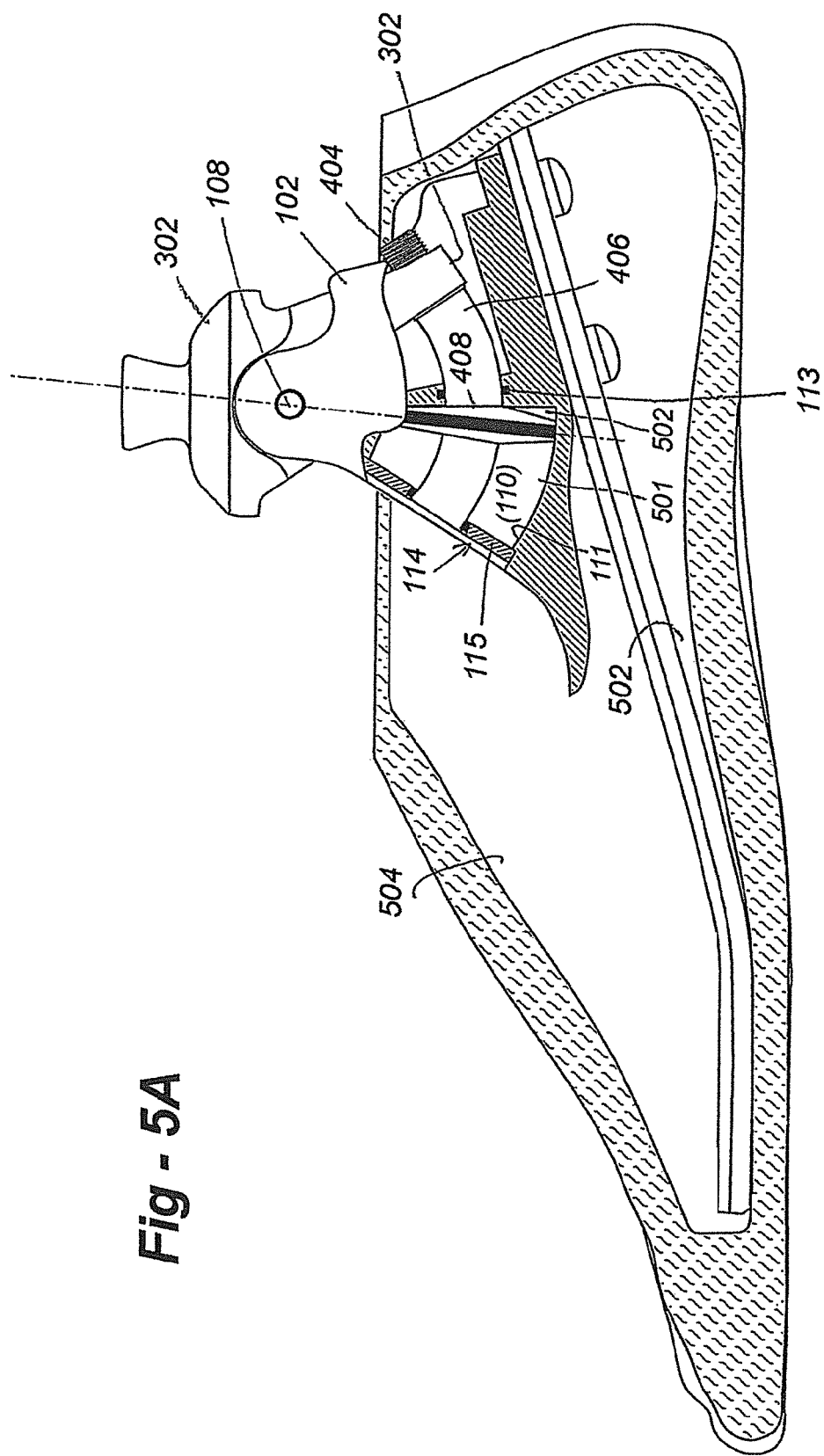

PROSTHETICS USING CURVED DAMPENING CYLINDERS

FIELD OF THE INVENTION

This invention relates generally to prosthetics and, in particular, to artificial joint and limbs utilizing curved dampening cylinders to reduce component count and wear.

BACKGROUND OF THE INVENTION

Those who wear prosthetic legs or feet confront several challenges to achieve natural and comfortable walking. These issues include changes in "effective heel height" and changes in the slope of the terrain encountered. Artificial limbs may function properly over smooth, horizontal surfaces or on slight inclines, but steeper inclines present problems, particularly when walking downhill. If the angle of the foot is not adequately adjustable, only the heel may make ground contact, making it difficult to accommodate the user's body weight and avoid buckling of the knee. For this reason, many prosthesis wearers often choose to walk sideways when walking downhill.

Manual, mechanical adjustments are often difficult to set or calibrate, and do not automatic adjust for changes in heel height or varying terrain slope. To address these deficiencies, various self-adjusting structures have been introduced over the years. One improvement has been in the development of damping mechanisms, some involving hydraulics. An early example is U.S. Pat. No. 2,470,480, which describes an artificial foot having hydraulic cushioning means between the ankle and the sole plate. A needle value is provided for controlling the passage of hydraulic fluid so that the walking action can be adapted to a particular person.

U.S. Pat. No. 6,855,170 resides in a foot connected to a leg prosthesis via a pivot axle such that the angular position between the foot and the leg prosthesis is adjustable to a desired angular position. This is accomplished with a piston displaceable in a cylinder attached to the leg prosthesis. A two-way valve permits the flow of medium between the two chambers in the cylinder. The two-way valve is adjustable with a control stick operable from the outside of the prosthesis. One problem with this design is that the hydraulic cylinder is oriented along the foot, resulting in a bulky structure.

To achieve a more compact design, U.S. Pat. No. 7,985,265 describes a prosthetic ankle and foot combination wherein the hydraulic cylinder is oriented along the leg as opposed to the foot. This device has an ankle joint mechanism constructed to allow damped rotational movement of a foot component relative to a shin component. The mechanism provides a continuous hydraulically damped range of ankle motion during walking with dynamically variable damping resistances, and with independent variation of damping resistances in the plantarflexion and dorsiflexion directions. Single and dual piston hydraulic damping arrangements are disclosed, including arrangements allowing independent heel-height adjustment.

Although the solution described in the '265 patent achieves a more compact package, it suffers from the same drawback as other prostheses that utilize a conventional hydraulic cylinder; namely, since the ankle rotates and the cylinder is straight, some form of linkage must be includes to convert pivoting motion to reciprocal. These linkages need pivot axes of their own, resulting in more moving parts and places where wear can occur.

SUMMARY OF THE INVENTION

This invention resides in prosthetic joint and limb components that utilize a single, curved dampening cylinder to reduce component count and wear. An embodiment associated with a prosthetic foot/ankle requires only three major components; namely, a housing adapted for coupling to a foot blade, an ankle component adapted for coupling to a pylon, and a piston that moves within a curved cylinder in the housing during ambulation.

The ankle component is pivotally attached to the housing at the center of curvature of the cylinder. The piston defines front and rear, variable volume chambers in the cylinder. The chambers are in fluid communication with one another via valves and internal ports, such that fluid is exchanged between the chambers to control dampening as the ankle pivots between plantarflexion and dorsiflexion.

In the preferred embodiment the fluid is a hydraulic fluid, and the housing, ankle component, rod and piston portion are made from precisely machined metal. A first, one-way check valve is used to direct the flow of fluid from the rear chamber to the front chamber during plantarflexion. A second, one-way check valve is used to direct the flow of fluid from the front chamber to the rear chamber during dorsiflexion. Independently adjustable flow-control valves in line with each check valve are used to establish and maintain desired levels of dampening during plantarflexion and dorsiflexion, including different levels of dampening in each direction. In the preferred embodiment, the flow-control valves are spool valves adjusted via rotation.

BRIEF DESCRIPTION OF THE DRAWINGS

FIG. 1C is a central cross section of the housing;

FIG. 1D is a cross section of the housing showing a fluid port;

FIG. 2A is a first oblique drawing of one of the two spool valves that seats into the housing;

FIG. 2B is a second oblique drawing of the spool valve of FIG. 2A;

FIG. 5A is an assembly drawing including the housing, ankle component and piston component in a neutral condition;

DETAILED DESCRIPTION OF THE INVENTION

This invention resides in prosthetic joint and limb components that utilize a single, curved dampening cylinder to reduce component count and wear. In contrast to devices that rely on linear cylinders, the invention requires only one pivoting axis without the need for link members that rotate about additional axes. Such link members not only increase part count, the movement and potential play of the additional moving parts may result in added expense and increased wear.

In an embodiment associated with a prosthetic foot/ankle requires only three major components: a housing, an ankle component, and a piston component. These major components are in addition to a few minor components and the foot blade to which the housing attaches and the plyon to which the ankle component attaches. Foot blades and pylons are well known to those of skill in the art, and the invention is not limited in terms of which foot blades, pylons, or associated coupling mechanisms are used.

Figure 1A:
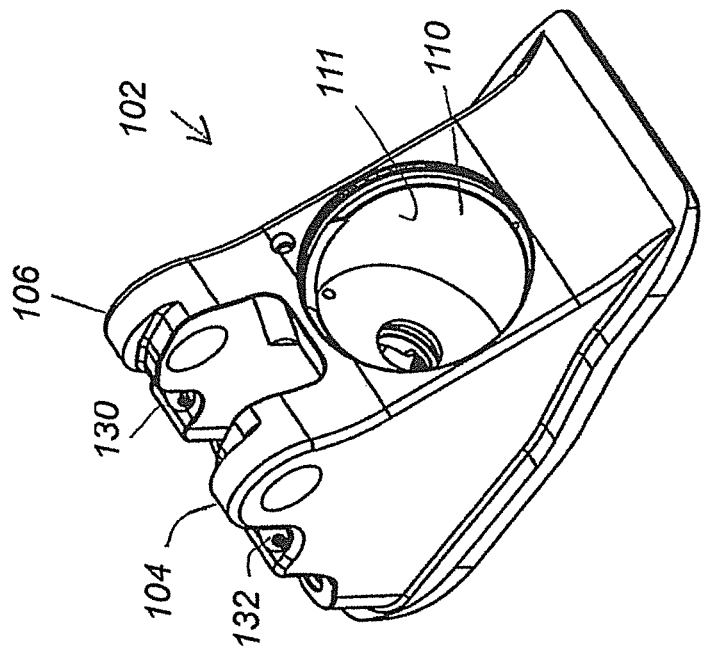
FIG. 1A is a first oblique drawing of a housing according the preferred embodiment seen from a frontal perspective.
Figure 1B:
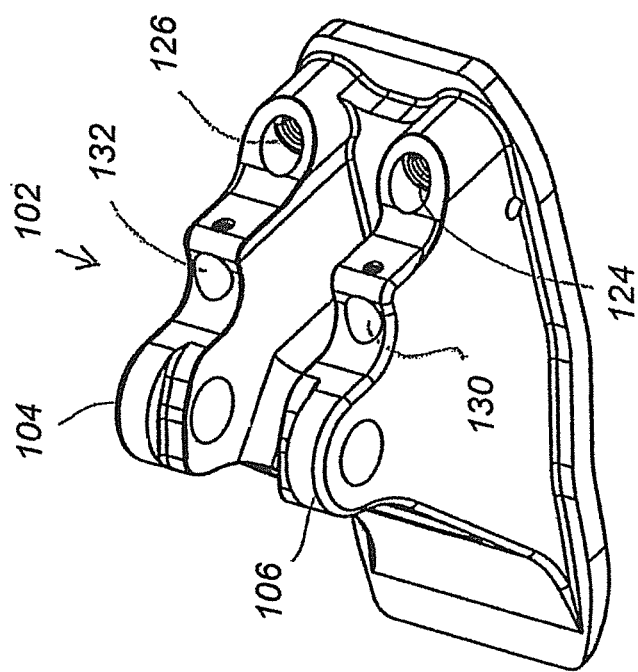
FIG. 1B is a second oblique drawing of the housing viewed from a rear perspective.

FIGS. 1A and 1B are oblique drawings of the housing seen from different perspectives, and FIG. 1C is a central cross section of the housing. The major components are preferably fabricated form metal, though conceivably ceramics or hard plastic materials may be substituted. In the preferred embodiment, the housing is fabricated from aluminum to keep weight down, whereas the other major components are stainless steel. Modern, computer-controlled machining processes may be used to form all of the major components, including the curved cylinder and curved piston, with tolerances sufficient to achieve extended operation.

The housing 102 includes upper arms 104, 106, each with a through bore defining a pivot axis 108. A curved cylinder 110 is formed within the housing 102 having a circular radius of curvature concentric to the pivot axis. The centerline of the cylinder lies in a plane orthogonal to the pivot axis, and the cylinder has a circular cross section taken along radii from the pivot axis. In one specific embodiment, the diameter, D, of the curved cylinder is 1.88 inches, +/−, and the radius of curvature, R, is 1.25 inches, +/−.

The back of the cylinder 110 includes an aperture 112 that seals against a rod portion of the piston component as the ankle component moves. The front of the cylinder includes an opening 113 to receive a cover 114 having a second aperture 116 that seals against a different portion of the piston rod as explained in further detail below. Once the piston component is installed in the cylinder, the cover 114 is installed over the opening 113 with appropriate seals to ensure fluid containment.

The bottom surface of the housing includes a surface 120 that connects to a foot blade shown the assembly drawings of FIG. 5. Multiple threaded fasteners may be used to provide a secure connection between the housing and the foot blade, with the cross section of FIG. 1C showing one such connection at 122. Threaded holes 124, 126 in FIG. 1B are associated with two additional fasteners.

Figure 1F:
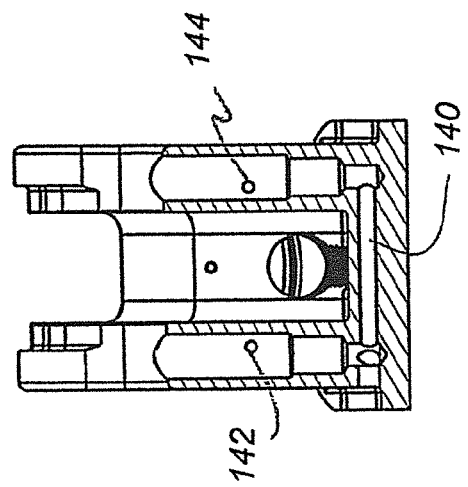
FIG. 1F is a cross section of the housing illustrating the fluid communication between the first and second valves cavities.
Figure 1E:
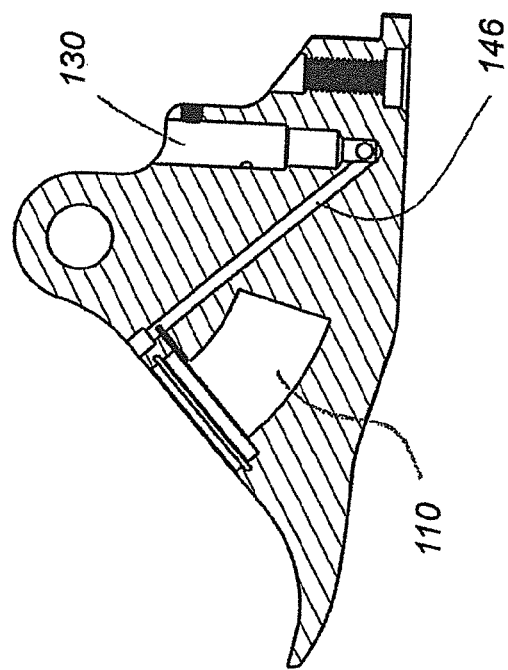
FIG. 1E is a cross section of the housing showing a different fluid port.

The housing includes two cavities 130, 132, each configured to receive a valve assembly including a one-way check valve and spool valve of the type depicted in FIG. 2. As shown in the partial cross section of FIG. 1F, the upper portion of each cavity is in communication with the rear chamber of the cylinder 110 through ports 142, 144. FIG. 1D shows the port to the rear chamber associated with cavity 130. The bottom portions of the cavities are in communication with one another through port 140, and further in communication with the front chamber of the cylinder through port 146, depicted in the cross section of FIG. 1E, also through cavity 130 but offset from the cross section of FIG. 1D.

Figure 1G:
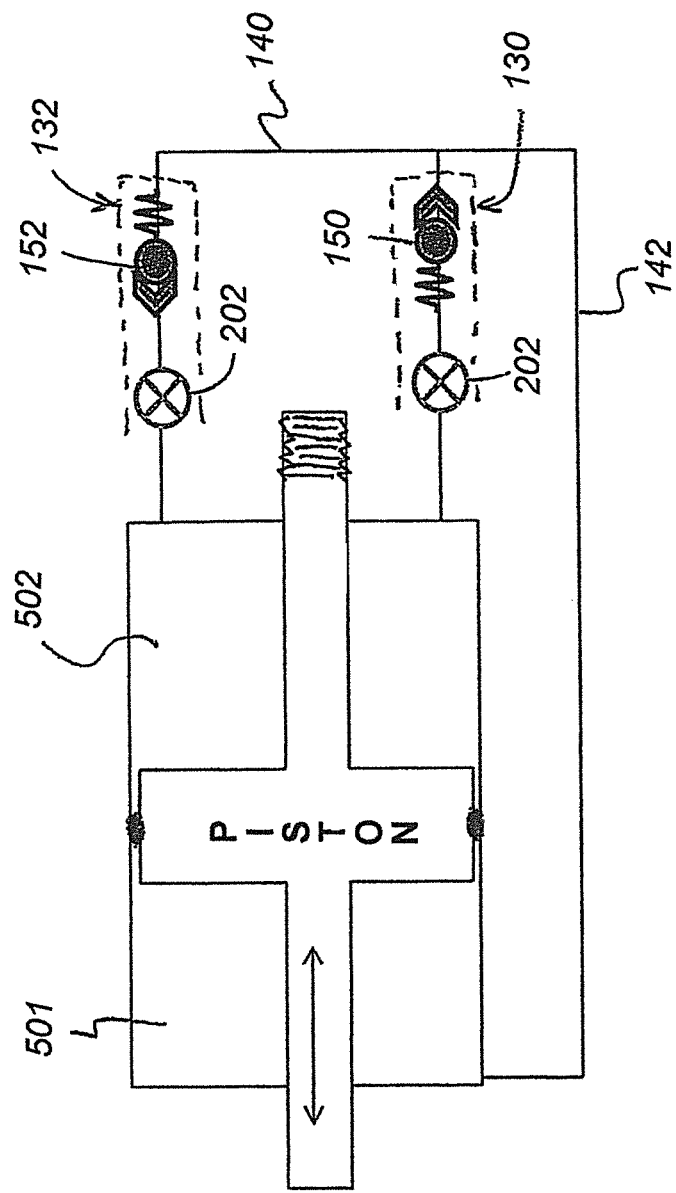
FIG. 1G is a simplified schematic diagram illustrating the hydraulic circuit.

FIG. 1G is simplified diagram of the hydraulic circuit. Cavity 130 includes a spool valve 202 and a one-way, spring-biased check valve 150 that allows fluid to travel from the forward chamber 501 through port 142 and into the rear chamber 502 during plantarflexion. Cavity 132 includes a spool valve 202 and a one-way, spring-biased check valve 152 that allows fluid to travel from the rear chamber 501 through ports 140, 142 and into the front chamber 502 during dorsiflexion. The flow of fluid set by the spool valves 202 independently control the degree of dampening in the two directions.

FIG. 2A is a first oblique drawing of one of the two one-way valves 202 that seats into the housing, and FIG. 2B is a an oblique drawing of the one-way valve of FIG. 2A seen from a different perspective. Each of the two valves are identical, and each includes a sleeve 204 with graduated perforations 206. A rotatable part 208 moves in and out of the sleeve to determine which of the perforations are used to determine flow control through that valve. The one-way valves (not shown), are installed the respective cavities 130, 132, followed by the spool valves with the rotatable parts 208 exposed for flow setting. Note that either of the cavities 130, 132 may be used for plantar-dorsiflexion depending upon the way in which the check valve is installed for that cavity.

Figure 3B:
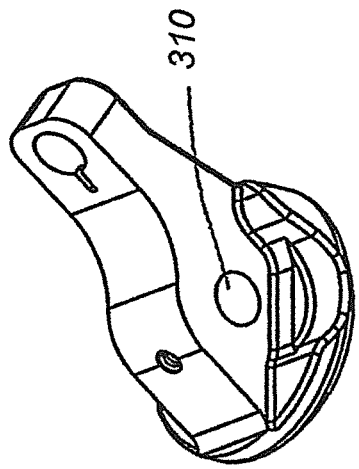
FIG. 3B is a second oblique drawing of the ankle component viewed from a different perspective.
Figure 3A:
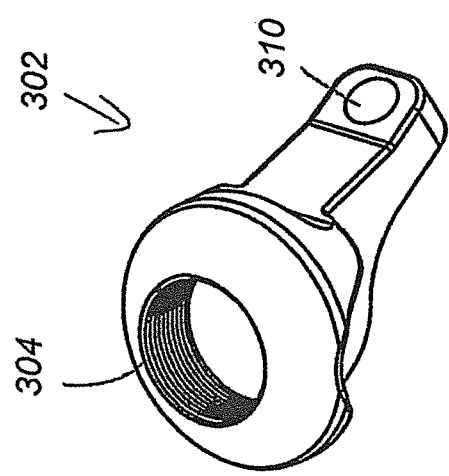
FIG. 3A is a first oblique drawing of an ankle component according the preferred embodiment seen from a first perspective.
Figure 3C:
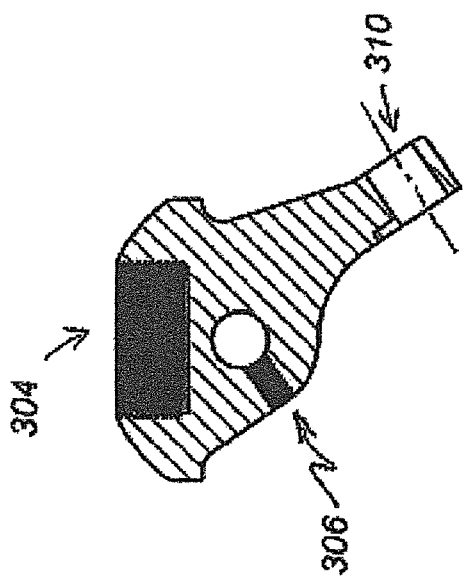
FIG. 3C is a central cross section of the ankle component.

FIG. 3A is a first oblique drawing of a preferred ankle component. FIG. 3B is a different view of the component, and FIG. 3C is a central cross section. The component 302 includes an upper threaded opening 304 to receive a pylon (not shown). The component further includes a through-bore having an axis 108 which corresponds to the central pivot axis of the housing 102, such that the ankle component rotates on axis 108 in a plane parallel to the circular axis of the cylinder 113.

Figure 4C:
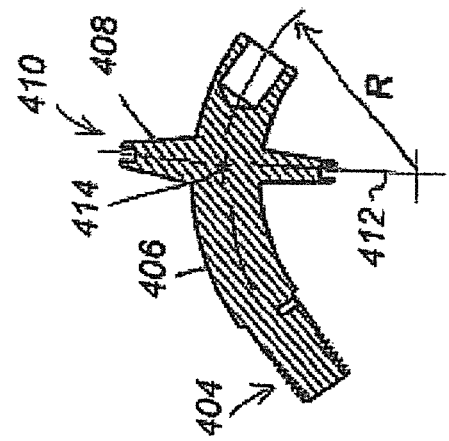
FIG. 4C is a central cross section of the piston component.
Figure 4B:
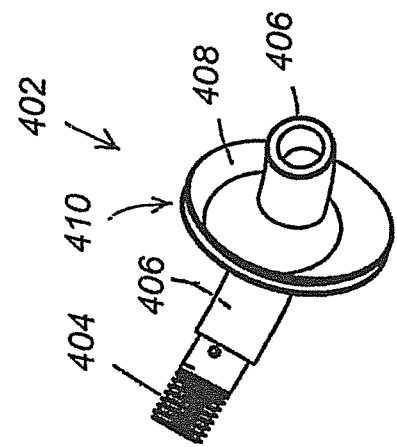
FIG. 4B is a second oblique drawing of the piston component viewed from a different perspective.
Figure 4A:
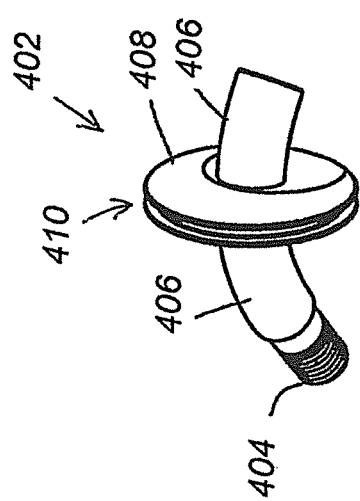
FIG. 4A is a first oblique drawing of a piston component according the preferred embodiment seen from a first perspective.

As seen in the cross section of FIG. 3C, a threaded port 306 is optionally provided to receive a bolt or set screw (not shown) to lock the ankle component in position relative to the housing. The ankle component further includes a second bore 310 to receive the threaded end 404 of piston component 402 illustrated in FIG. 4. FIG. 4A is a first oblique drawing of the piston component, FIG. 3B is a different view of the component, and FIG. 3C is a central cross section.

The piston component 402 includes a rod portion 406 with an integrally formed, flared section 408. The flared section 408 includes an outer, peripheral groove 410 configured to receive a multipart Teflon ring that seals the flared section against the inner wall of the cylinder as the piston moves within the cylinder. The curve of the rod portion 406 preferably has a centerline coextensive to that of the cylinder, with the plane 412 of the flared section being orthogonal to the centerline at point 414.

FIG. 5A is an assembly drawing including the housing, ankle component and piston component in a neutral condition. These drawings illustrate the ankle component coupled to the housing such that is rotates about the single axis 108. Also shown is the way in which the rear portion ankle component 302 is coupled to the threaded portion 404 of the piston rod 406, resulting in a solid mechanical connection. The rear seal between the piston rod 406 and the aperture 112 through the housing is shown at 113. The front plate 114 has been installed with seals being depicted at 115. The housing is attached to a suitable foot blade 502, and a pliant foot form is shown at 504. The flared portion 408 is sealed against the inner wall 111 of cylinder 110, establishing a front chamber 501 in front of the flared portion 408 of the piston and a rear chamber 500 behind the flared portion. The volumes of the front and rear chambers 501, 500 are not fixed, but rather vary through ambulation.

Figure 5B:
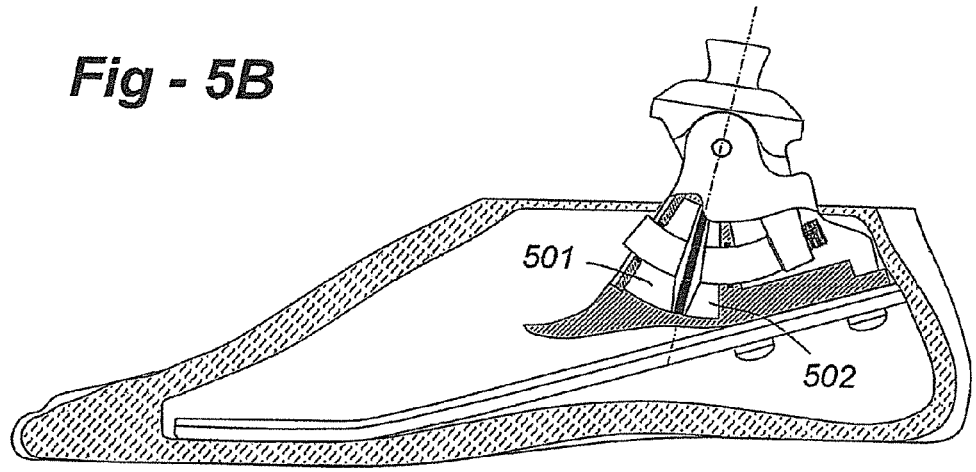
FIG. 5B is an assembly drawing at 8 degrees of plantarflexion.
Figure 5C:
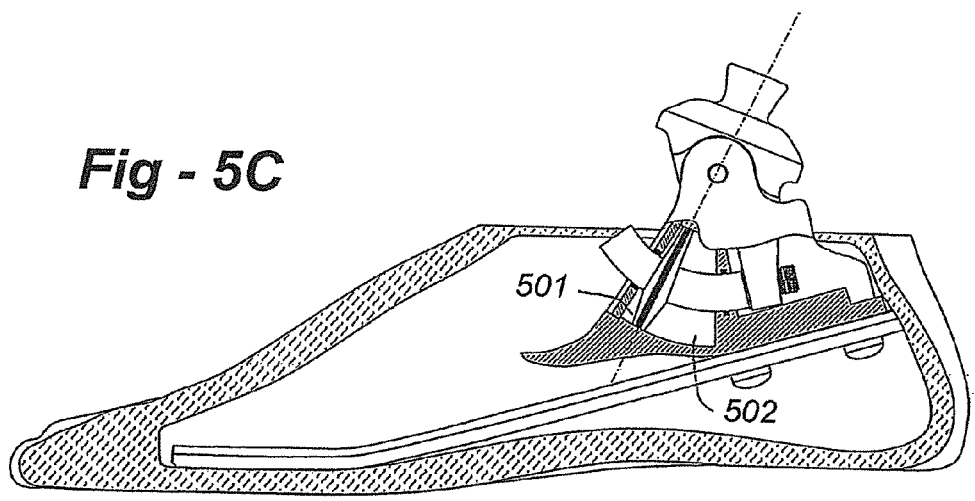
FIG. 5C is an assembly drawing at 18 degrees of plantarflexion.

In the neutral position shown in FIG. 5A, the front chamber 501 is of maximum volume, whereas the volume of rear chamber 500 is at its minimum. FIG. 5B depicts the assembly at 8 degrees of plantarflexion, and FIG. 5C is 18 degrees of plantarflexion. As the ankle component pivots backwardly during plantarflexion, the piston rotates forwardly in the cylinder, expelling fluid from the front chamber 501 to the rear chamber 500 through the one-way valve installed at 132. The dampening of the motion is established and controlled by the flow rate setting of the valve. As dorsiflexion begins, the fluid is transferred from the rear chamber 500 back into the forward chamber 501, with the level of dampening being independently controlled by the flow rate setting of the other valve.

The apparatus just described offers numerous advantages in addition to its elegant simplicity and few moving parts. In contrast to previous designs which use linear cylinders and achieve a limited range of motion (ROM) on the order or 7-9 degrees, the assembly achieves 18 degrees. While passive dampening is used to exchange fluid between the forward and rear chambers, in alternative embodiments the prosthesis may be instruments with angular or other position sensors, with the on-way valves being replaced with active fluid pressurization and suction being used as part of an active, electromechanical system. Fluids other than hydraulic fluids may be used including gaseous fluids including air, and the design is applicable to other joints that pivot substantially in a plane such as the knee.

The invention claimed is:

1. A prosthetic ankle, comprising: a housing for coupling to a foot blade having an upper portion with a pivot axis; a curved cylinder in the housing; the curved cylinder having a central, circular radius of curvature to the pivot axis, the centerline of the cylinder lying in a plane orthogonal to the pivot axis and having a circular cross section as measured along a radius extending from said pivot axis; an ankle component adapted for coupling to a pylon coupling, the ankle component being pivotally attached to the housing at the center for curvature of the cylinder; a piston disposed within said curved cylinder so as to define a front and a rear variable volume chamber within the cylinder, said front variable volume chamber being defined by a first face of said piston and a first portion of said curved cylinder and said rear variable volume chamber being defined by a second face of said piston and a second portion of said curved cylinder, said front and rear chamber being in fluid communication with one another; and a curved rod having a centerline coextensive with the centerline of the cylinder; the curved rod mechanically engages said ankle component, said curved rod extending into said curved cylinder so as to engage said piston; said curved cylinder including a back portion having a first opening which seals against a first portion of said curved rod so as to allow said rod to pass therethrough, and establish a mechanical linkage between said ankle component and said piston, and a front portion having a second aperture therein which seals against a second portion of said curved rod so as to allow said rod to pass therethrough; whereby fluid is exchanged between the front and rear chambers to control dampening as the ankle pivots between plantarflexion and dorsiflexion.

2. The prosthetic ankle of claim 1, wherein the fluid is a hydraulic fluid.

3. The prosthetic ankle of claim 1, wherein the housing, ankle component, rod and piston portion are metal.

4. The prosthetic ankle of claim 1, further comprising:
a port within the housing that fluidly interconnects the front and rear chambers;
a first, one-way check valve and a flow valve in line with the port to control dampening during plantarflexion; and
a second, one-way check and a flow valve in line with the port to control dampening during dorsiflexion.

5. The prosthetic ankle of claim 4, wherein the flow valves are independently adjustable spool valves to establish and maintain desired levels of dampening during plantarflexion and dorsiflexion.

6. The prosthetic ankle of claim 5, wherein each spool valve includes an insert with graduated perforations, such that rotation of the insert varies the flow of fluid through that valve.

7. A prosthetic ankle, comprising:
a housing having an upper portion with a pivot axis and a lower portion adapted for coupling to a foot blade;
a curved cylinder having an inner wall defining a cross section within the housing, the cylinder having a central, circular radius of curvature concentric to the pivot axis, the centerline of the cylinder lying in a plane orthogonal to the pivot axis and having a circular cross section as measured along a radius extending from said pivot axis;
an ankle component having an upper portion adapted for coupling to a pylon;
the ankle component being configured to pivot with respect to the housing on the pivot axis;
the ankle component being further coupled to a curved rod disposed within the curved cylinder, the curved rod having a centerline coextensive with the centerline of the cylinder;
the curved rod including a single piston portion with an outer, peripheral seal against the inner wall of the cylinder, the peripheral seal defining front and rear, variable volume sealed chambers within the cylinder;
a port within the housing that fluidly interconnects the forward and rear chambers;
a first, one-way check valve and a flow valve in line with the port to control dampening during plantarflexion; and
a second, one-way check and a flow valve in line with the port to control dampening during dorsiflexion.

8. The prosthetic ankle of claim 7, wherein the fluid is a hydraulic fluid.

9. The prosthetic ankle of claim 7, wherein the flow valves are independently adjustable spool valves to establish and maintain desired levels of dampening during plantarflexion and dorsiflexion.

10. The prosthetic ankle of claim 9, wherein each spool valve includes an insert with graduated perforations, such that rotation of the insert varies the flow of fluid through that valve.

11. The prosthetic ankle of claim 7, wherein the housing, ankle component, rod and piston portion are metal.

12. The prosthetic ankle of claim 7, wherein the piston portion includes a peripheral groove to receive the peripheral seal.

* * * * *